United States Patent [19]
Chan

[11] Patent Number: 5,624,184
[45] Date of Patent: Apr. 29, 1997

[54] BONE CEMENT PREPARATION KIT HAVING A BREAKABLE MIXING SHAFT FORMING AN OUTPUT PORT

[76] Inventor: Kwan-Ho Chan, 4803 1st Pl., Lubbock, Tex. 79416

[21] Appl. No.: 541,543

[22] Filed: Oct. 10, 1995

[51] Int. Cl.$^6$ ........................................ B01F 13/06
[52] U.S. Cl. ...................... 366/139; 366/189; 366/256
[58] Field of Search ............................ 366/130, 139, 366/189, 255, 256, 257, 258, 332, 333, 602; 206/219, 221

[56] References Cited

U.S. PATENT DOCUMENTS

| | | | |
|---|---|---|---|
| 4,197,967 | 4/1980 | Baur et al. | 366/256 X |
| 4,721,390 | 1/1988 | Lidgren | 366/139 |
| 4,758,096 | 7/1988 | Gunnarsson | 366/139 |
| 4,808,006 | 2/1989 | Kaufeler | 366/130 X |
| 4,973,168 | 11/1990 | Chan | 366/139 |
| 5,252,301 | 10/1993 | Nilson et al. | 366/256 X |
| 5,328,262 | 7/1994 | Lidgren et al. | 366/139 |

*Primary Examiner*—Charles E. Cooley
*Attorney, Agent, or Firm*—Pandiscio & Pandiscio

[57] ABSTRACT

A disposable telescoping mixing cartridge for mixing and delivering a quantity of bone cement. The cartridge cap includes a break-away agitator which opens an outlet port for the flow of cement. Therefore, the single opening serves as both an outlet port for the cement and the opening through which the agitator is reciprocated.

10 Claims, 11 Drawing Sheets

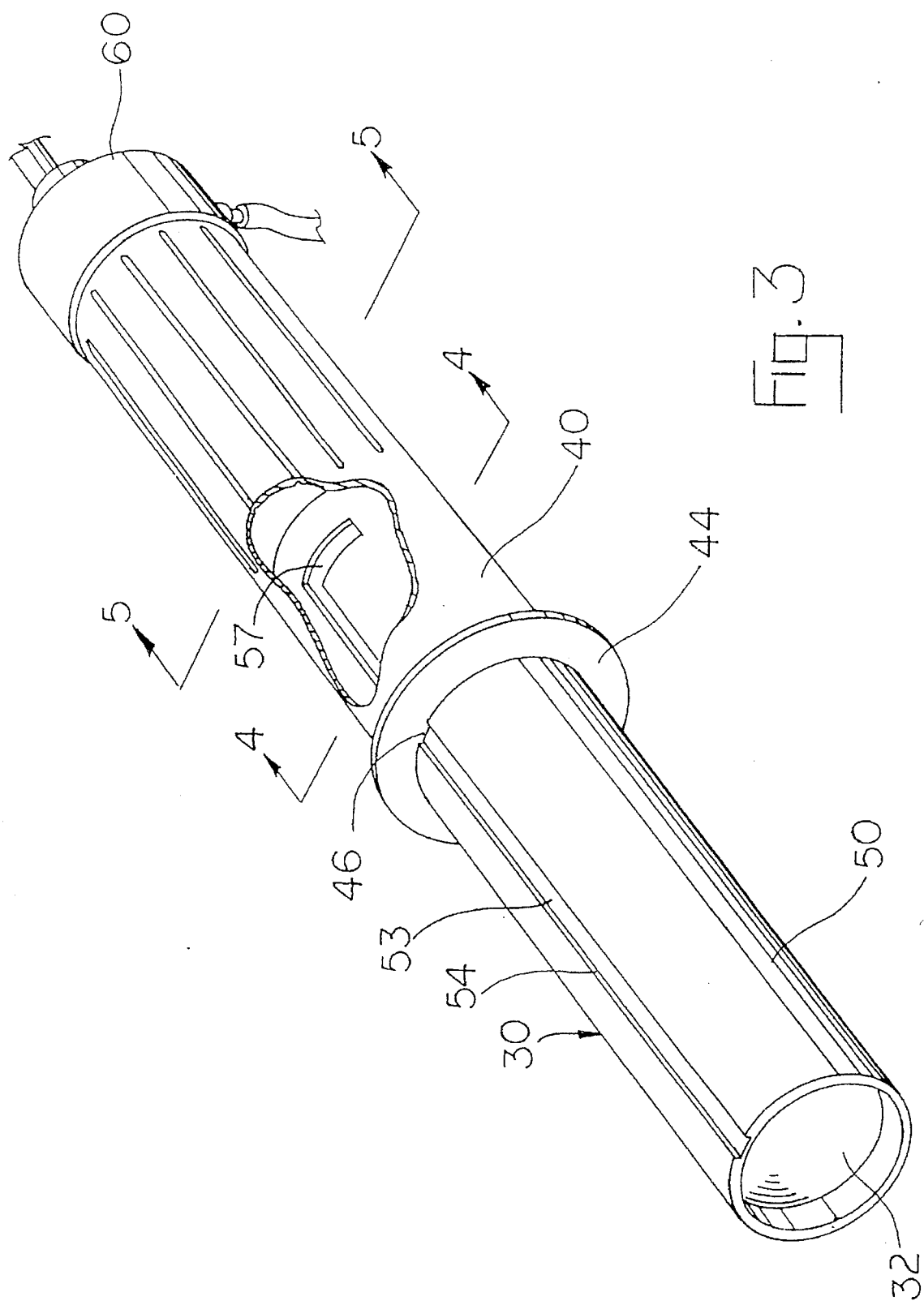

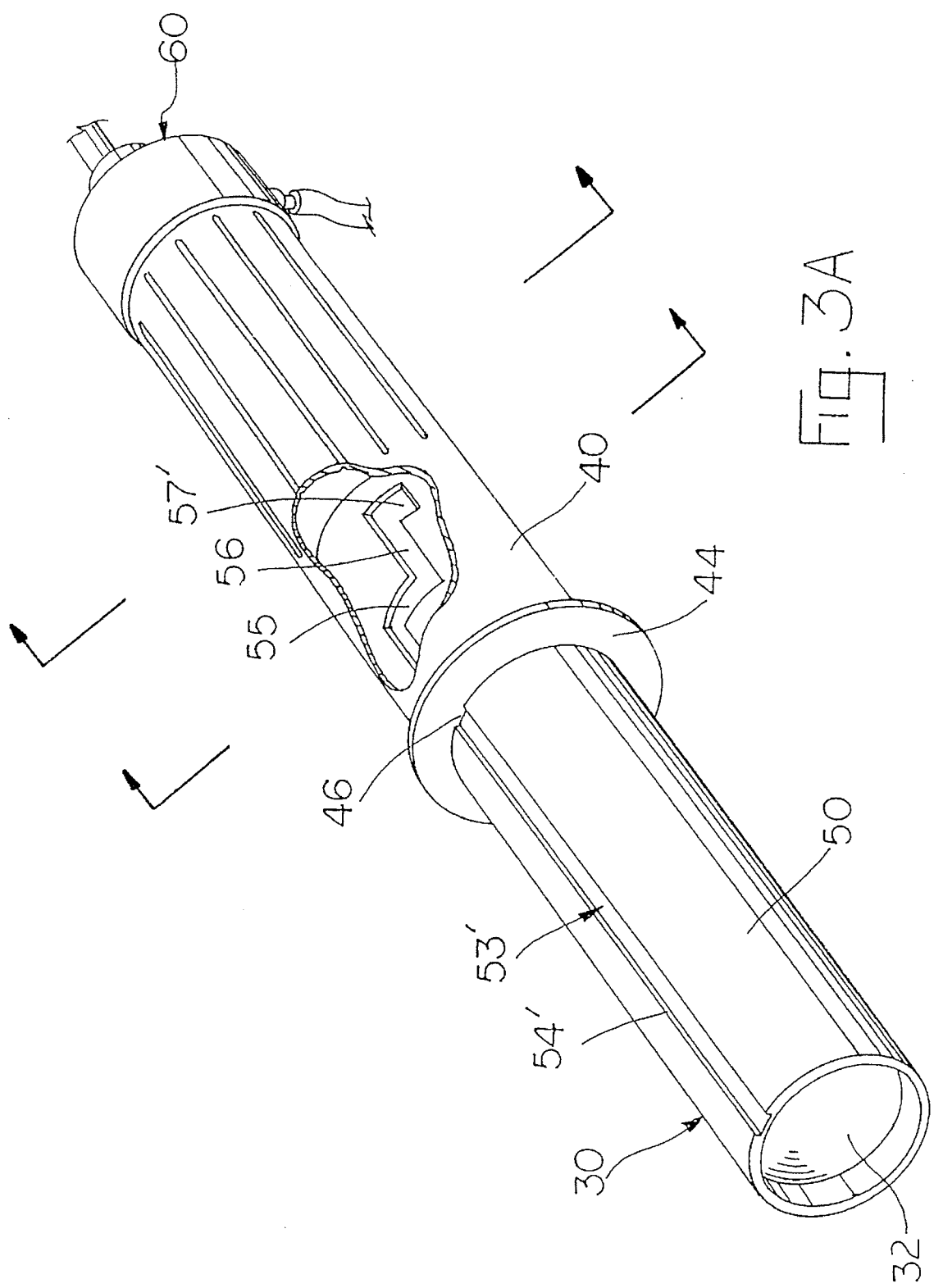

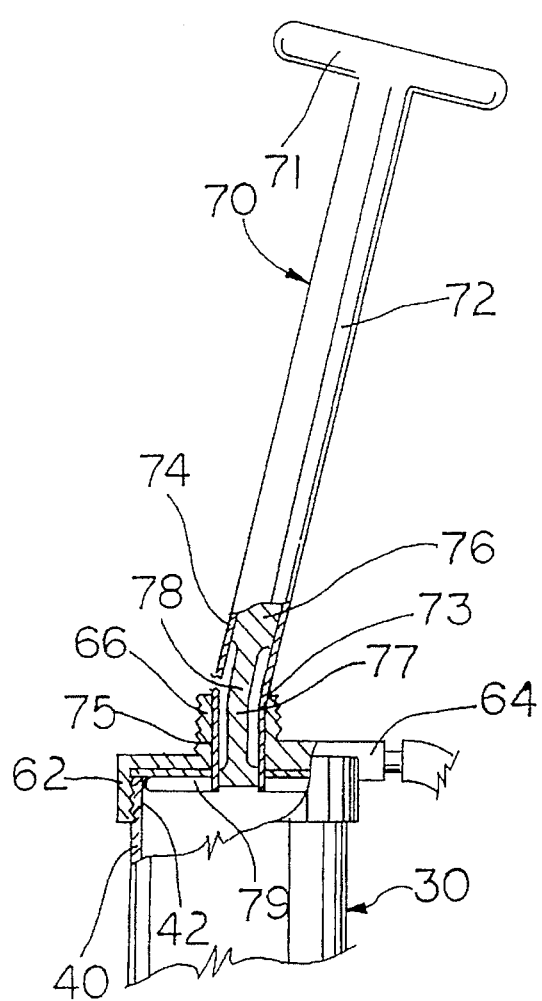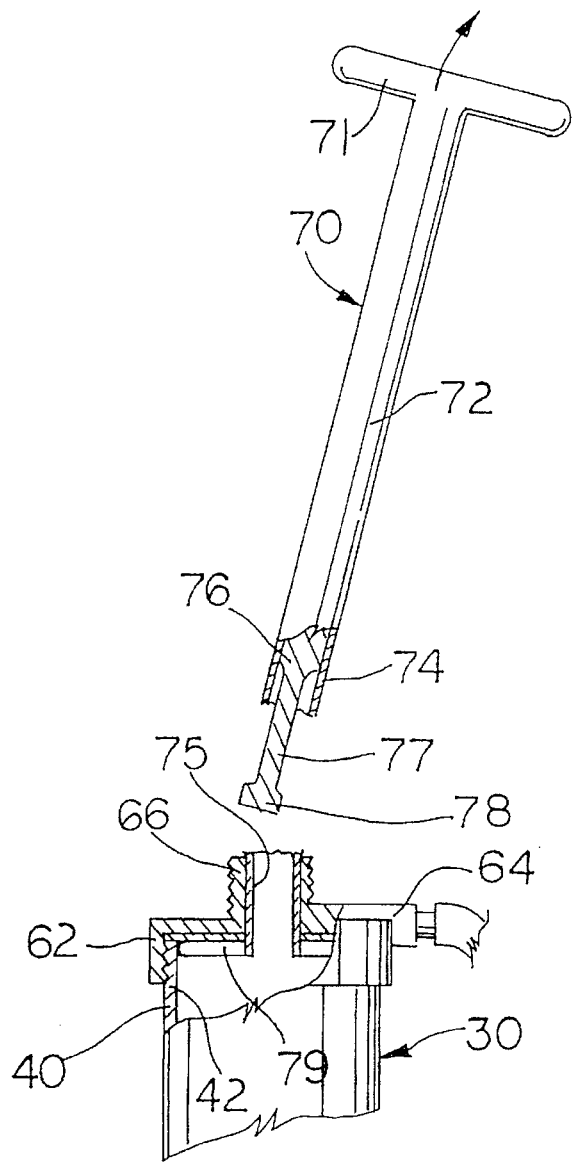

5,624,184

BONE CEMENT PREPARATION KIT HAVING A BREAKABLE MIXING SHAFT FORMING AN OUTPUT PORT

This invention relates to a disposable preassembled collection of preparation apparatus and various cement components used in the preparation of bone cement. The collection of disposable apparatus and constituent components being packaged as a single sterile kit for convenience and includes a telescoping mixing cartridge with a vacuum release mechanism and a break-away agitator. The break-away agitator forms an output for the ejection of the bone cement.

BACKGROUND OF THE INVENTION

In many orthopaedic surgical procedures, bone cements are used to fix implants to the bone. Conventional bone cements are generally polymeric materials, which are prepared by copolymerization of its components as needed. Bone cement is prepared by copolymerizing a liquid monomer and a powdered copolymer, such as methyl methacrylate and polymethyl methacrylate or methyl methacrylate-styrene. During mixing of the constituent components of the cement, air bubbles may be formed within the cement. It is thought that to improve the resultant strength of the cement, the air bubbles must be evacuated from the mixture to ensure a uniform reaction product. Consequently, the mixing of the constituent components is ideally performed in a vacuum.

The separate constituent components may be mixed within a mixing cartridge as is well known in the art. The mixing cartridge, when fully extended, provides a larger volume for mixing the constituent components to ensure that the constituent components are adequately mixed. Such mixing cartridges are generally enclosed by removable caps, which include a valved port for connection to a vacuum pump. Vacuum pumps draw a vacuum within the cartridges during the mixing process to reduce the occurrences of air bubbles within the cement. The caps have an off-set outlet port through which the mixed cement compound is expelled and a central opening through which an agitator is reciprocally disposed. The agitator has an elongated shaft and a mixing paddle for mixing the constituent components. The agitator shaft is broken off after mixing and the offset outlet port is opened to expel the cement. In a prior art vacuum cartridge mixing device, an end plunger is released after mixing yet while the cartridge is still under a vacuum. The vacuum pressure within the cartridge causes the plunger to be drawn into the cartridge to collect the cement. The plunger stops moving within the cartridge when the force exerted by the vacuum equalizes. After the cement is throughly mixed, the agitator shaft is broken off and the cartridge is inserted into a conventional cement applicator gun. Cement applicator guns are well known in the art. Generally, a variety of cement nozzles are affixed to the outlet port to aid in the application of the cement within the bone cavity. Because the outlet port is off center, a certain amount of cement cannot be expelled from the cartridge, and is discarded with the disposal of the cartridge.

Heretofore, the various cement constituent components and mixing apparatus have been individually packaged and provided to the user. Since the cement sets rapidly, the preparation and application of bone cement is time critical. Preparation of bone cement is generally performed in the sterile field of the operating room. Consequently, each piece of apparatus must be provided in a sterile package. Providing all of the various mixing apparatus and cement constituent components as a single preassembled collection or kit would be more convenient for the users in the operating room.

SUMMARY OF THE INVENTION

This invention provides a preassembled collection of disposable mixing apparatus and various cement constituent components needed for the preparation of bone cement in a convenient disposable kit. The kit includes a contoured storage tray, ampules of liquid cement monomer, packets of powder cement copolymer, a vacuum pump, connecting tubing with a vacuum indicator, a mixing cartridge, a cartridge cap and agitator, an assortment of connectable cement nozzles, and a funnel attachment. The kit can be packaged as a single unit for convenient and efficient use in the sterile environment of an operating room. In addition the contoured tray holds the various items in convenient positions to assist the user during the preparation of the bone cement. For example, the tray holds the mixing cartridge in a stable upright position so that the user does not have to hold the cartridge, leaving his hands free to operate the agitator or the vacuum pump.

The disposable telescoping mixing cartridge of the kit employs a vacuum release mechanism which releases the vacuum within the cement cartridge as the telescoping tubes are being compressed. The cartridge includes two telescoping tubular cylinders. The inner cylinder is shiftably received within the outer cylinder. The inner cylinder has an L-shaped longitudinal channel, and the outer cylinder includes a protrusion or key which is seated within the channel to provide for the lock and release of the inner cartridge relative to the outer cartridge. Alternatively, the channel may be stepped thereby allowing the inner cylinder to be rotated and axially moved within the outer cylinder between three selective positions: a fully extended mixing position, an intermediate vacuum release position, and a retracted applicator position.

The cartridge cap includes a break-away agitator which also serves as an outlet port after breaking. Therefore, the cap has a single opening to serve as both an outlet port for the cement and the opening through which the agitator is reciprocated. The agitator includes a handle and an elongated shaft reciprocally disposed within the outlet port of the cap. The shaft includes a tubular outer sleeve and an inner rod axially disposed within the sleeve. The sleeve has a frangible hollow distal end. Agitator paddles extend radially from the distal end of the sleeve for assisting in the mixing of the constituent components of the bone cement. The distal end of the rod terminates in an integral dumbbell shaped end plug. The small diameter of the middle segment of the dumbbell shaped end plug is positioned approximate to an annular notch formed in the sleeve. The distal end of the sleeve can be detached from the shaft so that the mixed cement compound can be expelled therethrough. The configuration of the dumbbell shaped end plug allows the rod to be bent at the middle section of the end plug while the sleeve is fractured at the notch. The hollow distal end of the sleeve remains seated within the outlet port of the cap to provide a passage for the mixed cement compound to be expelled.

Accordingly, an advantage of this invention is to provide a collection of disposable mixing apparatus and cement constituent components for vacuum mixing and cartridge delivery in a single sterile kit for convenient use.

Another advantage of this invention is that the tray included in the kit holds the mixing cartridge while the constituent components are mixed so that the cartridge does not have to be manually supported during the preparation of the cement compound.

Another advantage of this invention is that the telescoping mixing cartridge has a vacuum release mechanism which releases the vacuum during collapsing of the telescoping cartridge.

Another advantage of this invention is that the cap includes a single outlet port through which the agitator is reciprocated during the mixing process and cement is expelled during cement application.

Other advantages will become apparent upon a reading of the following description.

BRIEF DESCRIPTION OF THE DRAWINGS

A preferred embodiment of the invention has been depicted for illustrative purposes only wherein:

FIG. 3 is a perspective view of the mixing cartridge of this invention with a portion cut away to illustrate its vacuum release mechanism;

FIG. 3A is a perspective view of the mixing cartridge of this invention with a portion cut away to illustrate its two stage vacuum release mechanism;

FIG. 6 is a sectional view of the cap and breakaway agitator of this invention showing the dumbbell shaped end plug of the rod bent to sever the distal end of the outer sleeve;

FIG. 7 is a sectional view of the cap and breakaway agitator of this invention showing the shaft and dumb bell shaped end plug withdrawn from the distal end of the sleeve;

DESCRIPTION OF THE PREFERRED EMBODIMENT

The preferred embodiments herein described are not intended to be exhaustive or to limit the invention to the precise forms disclosed. Rather, they are chosen and described to best explain the invention so that others skilled in the art might utilize their teachings.

Figure 1:
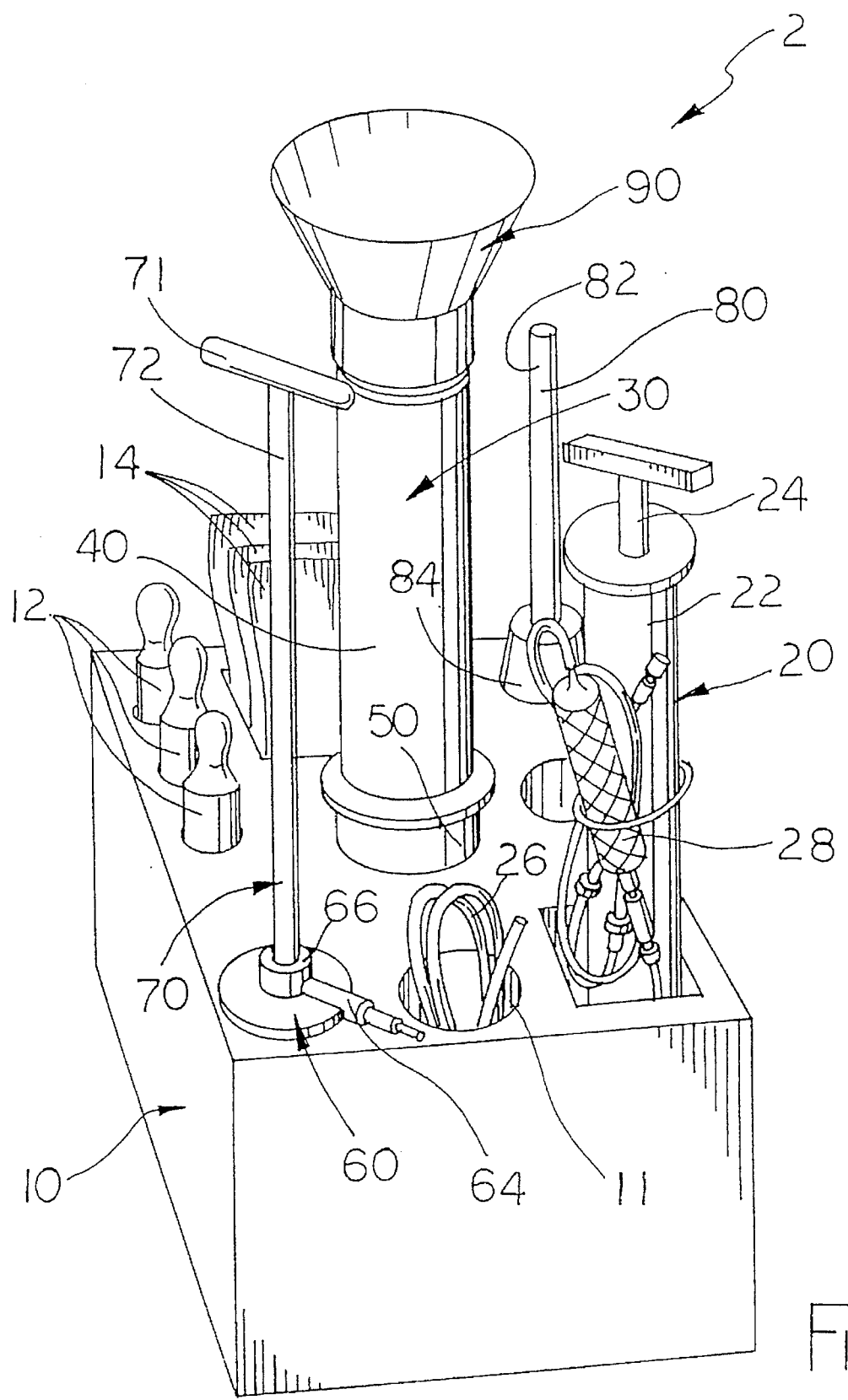
FIG. 1 is a perspective view of the kit of this invention.

FIG. 1 shows the collection of disposable items of kit 2 of this invention for use in the preparation of bone cement. Kit 2 consists of the following items: a contoured storage tray 10, ampules 12 of liquid cement monomer, packets 14 of powdered cement polymer, vacuum pump 20, connecting tubing 26 having a vacuum indicator 28, a mixing cartridge 30, a cartridge cap 60 and break-away agitator 70, an assortment of connectable cement nozzles 80, and a funnel attachment 90. Preferably, tray 10 is constructed from a molded plastic, which has a plurality of contoured recesses 11 (FIGS. 1, 8 and 9) within which the various mixing apparatus and constituent components 4 of the cements are stored. As shown in FIG. 1, tray 10 allows all of the kit items to be stored and packaged in a single sterile covering (not shown). Each of the kit items are held in their individual contoured recesses 11 formed in tray 10. In addition, tray 10 holds the various items at a convenient position to assist the user in preparing the bone cement. For example, tray 10 holds mixing cartridge 30 in a stable upright position so that the user does not have to hold the cartridge, leaving his hands free to pour in the constituent components, operate vacuum pump 20, or agitator 70.

Preferably, the constituent components 4 of the cements are individually packaged in premetered portions. The liquid monomer components are provided in ampules 12 and the powder copolymers are provided in sealed packets 14, although any suitable packaging for the components may be provided with the kit of this invention. Ampules 12 of the liquid monomer and packets 14 of powder copolymer are well known in the art and are commercially available from a variety of sources. Vacuum pump 20 uses a reciprocated piston design, although any suitable vacuum pump may be included as part of kit 2. Vacuum pump 20 includes a cylindrical body 22 and reciprocating shaft 24, which drives an internal piston (not shown). Vacuum pump 20 also includes a check valve (not shown) to permit air flow in one direction only through the pump orifice. The length of tubing 26 is used to connect pump 20 to cap 60 when connected to mixing cartridge 30. Preferably tubing 26 includes vacuum indicator 28. Vacuum indicator 28 is a plastic or rubber bulb, which collapses under the negative pressure of the vacuum drawn by pump 20.

Mixing cartridge 30 is preferably constructed of a disposable semi-transparent plastic, which allows the admixture of the constituent components 4 to be viewed. Cartridge 30 includes two telescoping tubular cylinders 40, 50. Both cylinders 40, 50 have open proximal and distal ends. Outer cylinder 40 axially receives inner cylinder 50 in a telescoping configuration. The outer diameter of inner cylinder 50 is concentrically seated against the inner diameter of outer cylinder 40. The outer peripheral surface of inner cylinder 50 is in a tight but not hermetically sealed engagement with the inner peripheral surface of outer cylinder 50 in a piston like manner. An air impermeable piston plug 32 is disposed within inner cylinder 50 approximate its distal end, so as to close the distal end of inner cylinder 50. Plug 32 is axially slidable within inner cylinder 50 for expelling the mixed cement compound 6 from cartridge 30 when the cartridge is connected to a cement gun.

Figure 2:
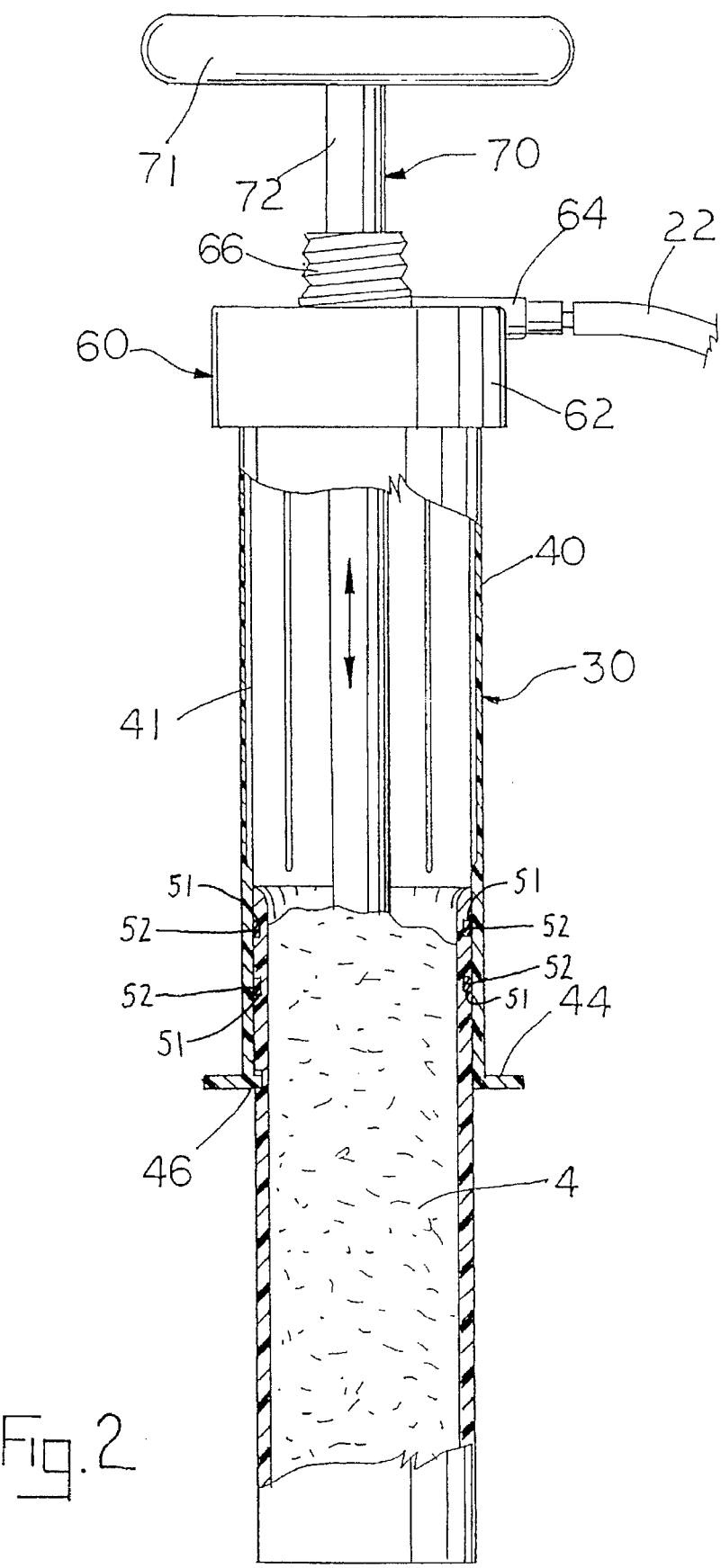
FIG. 2 is a side view of the mixing cartridge and the connected cap with a portion cut away to illustrate the mixing of the constituent components.
Figure 5:
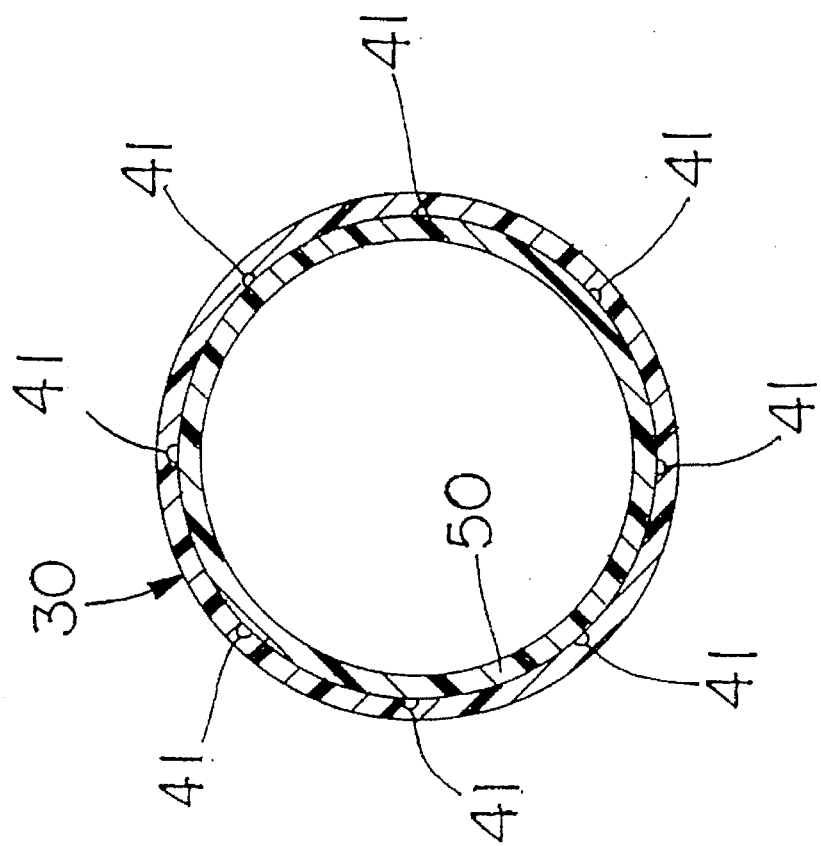
FIG. 5 is a sectional view of the mixing cartridge taken along line 5—5 of FIG. 3.
Figure 4:
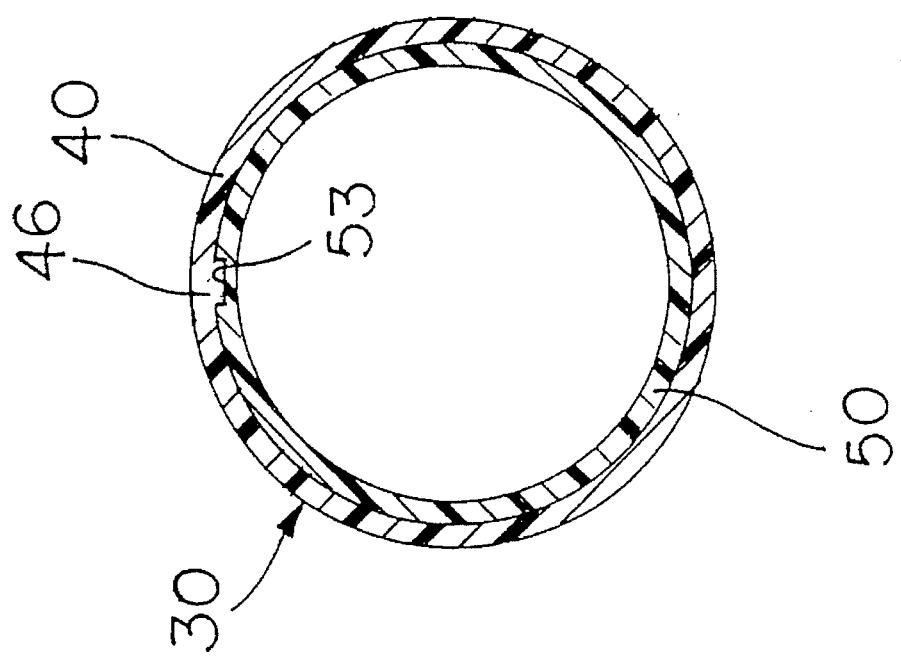
FIG. 4 is a sectional view of the mixing cartridge taken along line 4—4 of FIG. 3.

Outer cylinder 40 includes a threaded outer rim 42 adjacent its open proximal end. Threaded rim 42 allows connection of cap 60 and funnel attachment 90 to cartridge 30. While outer cylinder 40 is shown herein as including an outer thread rim, any suitable connection structure can be employed to provide the connection to funnel attachment and cap 60. Outer cylinder 40 also includes an annular end flange 44, which extends outwardly approximate its open distal end, and a block protrusion or key 46, which protrudes inwardly. As shown in FIGS. 2 and 5, the inner surface of outer cylinder 40 has a plurality of pressure evacuation grooves 41, which extend longitudinally from its proximal end.

Figure 10:
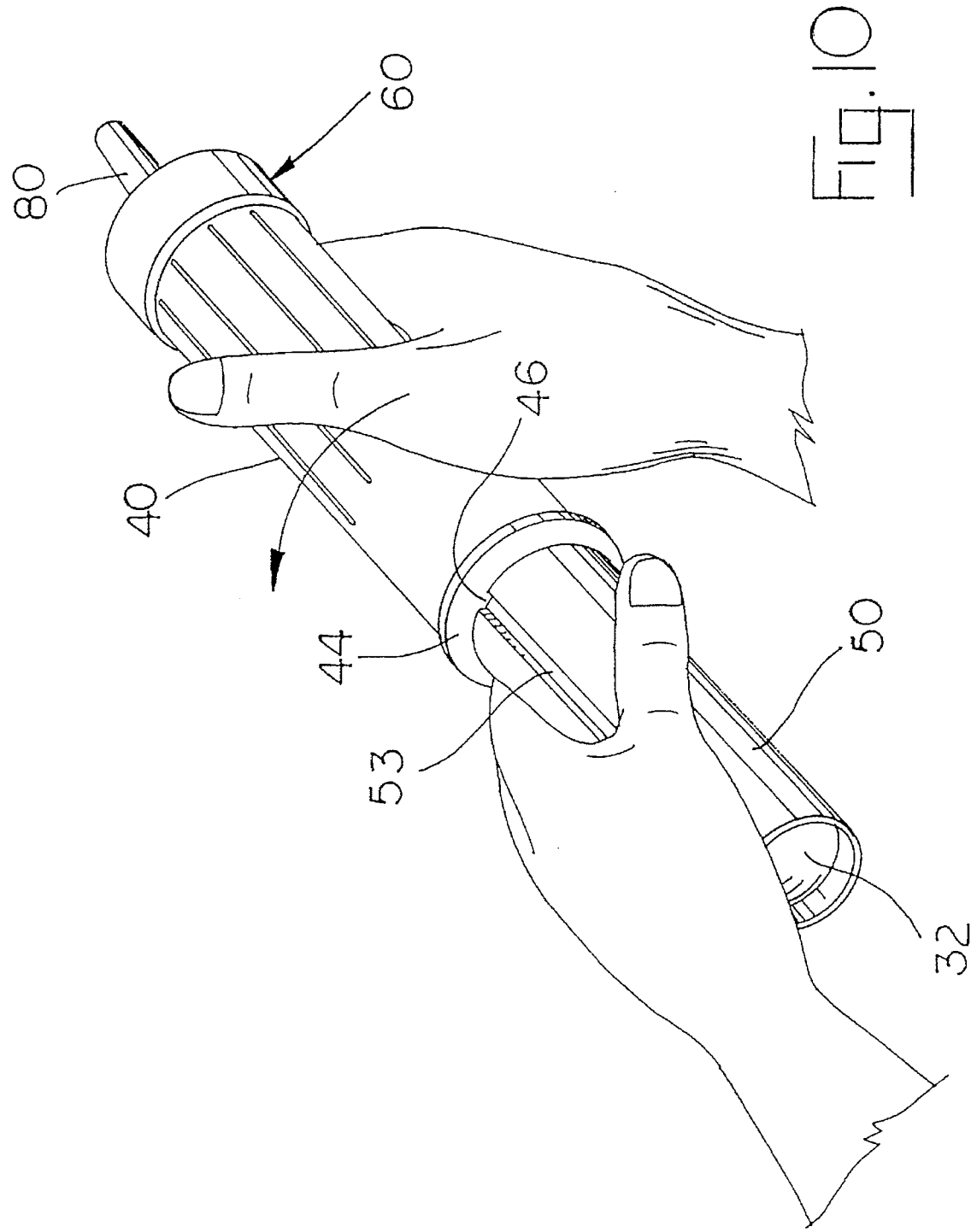
FIG. 10 is a perspective view of the mixing cartridge of this invention showing the manipulation of the inner cylinder within the outer cylinder to release the vacuum pressure and to collapse the cartridge.
Figure 11:
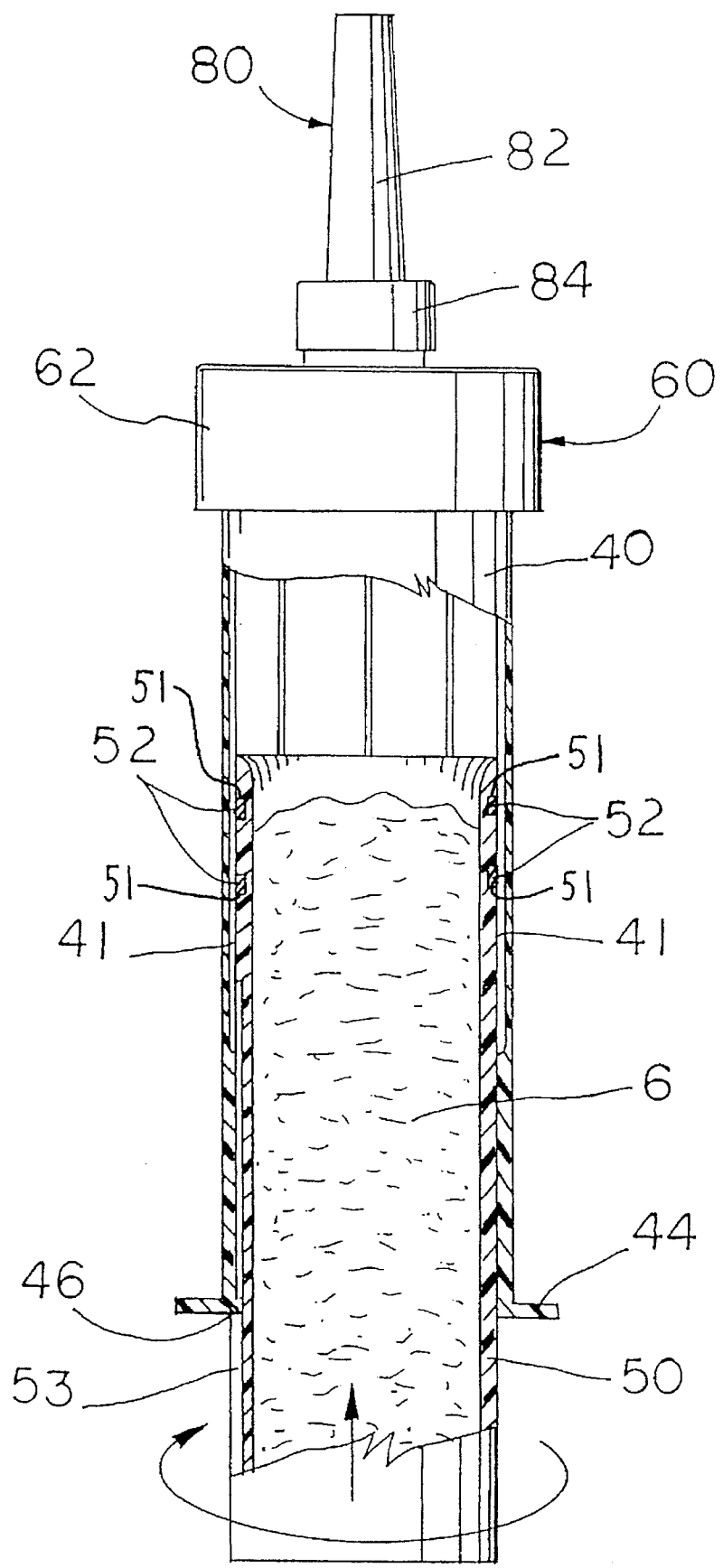
FIG. 11 is a side view of the mixing cartridge of this invention and a connected cement nozzle with a portion cut away to show the position of the inner and outer cylinders.

Inner cylinder 50 includes a pair of O-rings 52, which are seated within annular grooves 51 formed approximate its proximal end. O-rings 52 provide a hermetic seal between cylinders 40, 50. As shown in FIG. 3, inner cylinder 50 has an L-shaped longitudinal channel 53. Channel 53 includes a short lateral section 57 which connects to a major longitudinal section 54. The L-shaped channel allows the inner cylinder 50 to be rotationally and axially movable between two positions: a fully extended mixing position wherein key 46 is seated within lateral section 57, and a vacuum release and retracted position wherein the key is accommodated within the major longitudinal section. As shown in FIGS. 3, 10 and 11, key 46 of outer cylinder 40 is seated within channel 53 of inner cylinder 50. In an alternative embodiment, illustrated in FIG. 3A, the channel 53' is formed in a stepped configuration and includes a short intermediate lateral section 55', which connects the major longitudinal section 54' to the minor longitudinal section 56 and a short lateral end section 57'. Stepped channel 53' and key 46 provide a two stage vacuum release mechanism for cartridge 30. Stepped channel 53' allows inner cylinder 50 to be rotationally and axially moved between three positions: a fully extended mixing position, an intermediate vacuum release position, and a retracted applicator position.

As shown in FIGS. 2, 6 and 7, cartridge cap 60 includes an annular rim 62. The inner surface (not shown) of rim 62 is threaded to mate with the threaded rim 42 of outer cylinder 40 to provide a hermetically sealed connection over the proximal end of outer cylinder 40. Cap 60 includes a one way valve port 64, which is connectable to vacuum pump 20. Cap 60 includes a centered cement outlet port 66. The outer surface of cement port 66 is threaded to allow connection of cement nozzles 80 to cap 60.

As shown in FIGS. 6 and 7, agitator 70 includes a handle 71 and an elongated shaft 72 reciprocally disposed within outlet port 66 of cap 60. Shaft 72 includes a tubular outer sleeve 74 and an inner rod 76 axially disposed within sleeve 74. Shaft sleeve 74 is frangible and has a detachable distal end 75. Agitator paddles 79 extend radially from distal end 75 of shaft sleeve 74 for assisting in the mixing of the constituent components 4 of the bone cement. The distal end of inner rod 76 terminates in an integral dumbbell shaped end plug 78. The small diameter of the middle segment 77 of dumbbell shaped end plug 78 is positioned approximate to an annular notch 73 formed in shaft sleeve 74. As shown in FIGS. 6 and 7, distal end 75 of sleeve 74 can be detached from shaft 72 so that the mixed cement compound 6 can be expelled therethrough. When shaft 72 is withdrawn to its outer extreme from cartridge 30, paddles 79 abut against the inner wall of cap 60 and distal end 75 of sleeve 74 is fitted within outlet port 66 of cap 60. The configuration of dumbbell shaped end plug 78 allows rod 76 to be bent at middle section 77 of end plug 78 while sleeve 74 is fractured at notch 73. The hollow distal end 75 of sleeve 74 remains within outlet port 66 of cap 60 to provide a passage for the mixed cement compound 6 to be expelled.

Figure 7A:
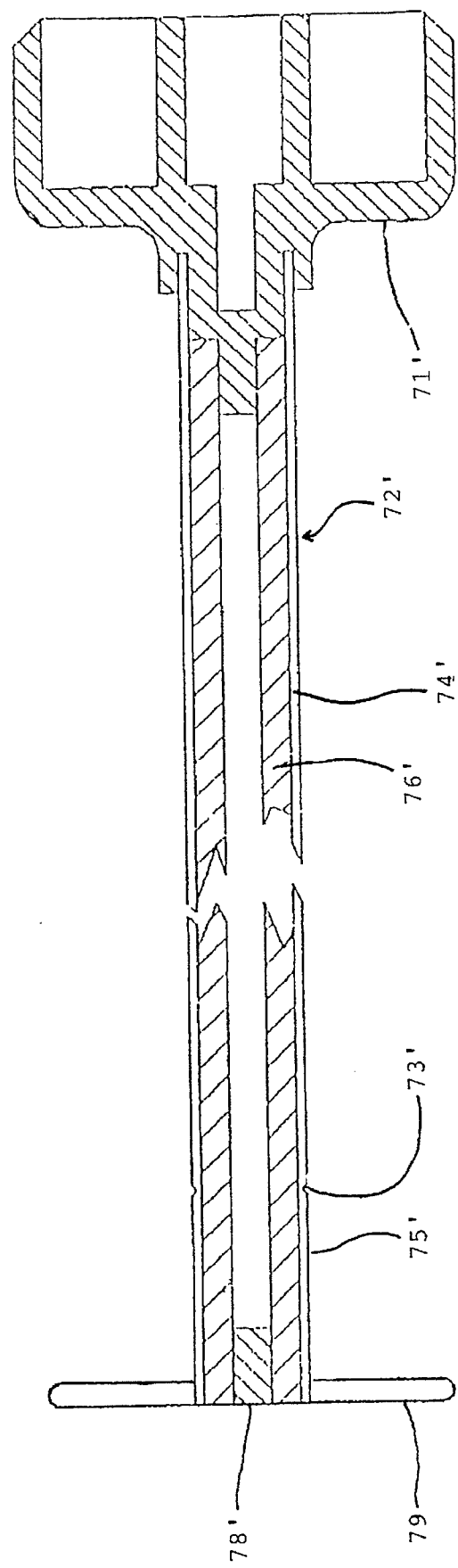
FIG. 7A is a sectional view of an alternative embodiment of the agitator of the invention.

An alternative embodiment of the break away sleeve 74 and dumbbell shaped distal plug is illustrated in FIG. 7A. As illustrated in FIG. 7A, elongated shaft 72' includes a tubular outer sleeve 74' and an inner rod 76' axially disposed within the sleeve. Shaft sleeve 74' is frangible and has a detachable distal end 75'. In the embodiment of FIG. 7A, the inner rod 76' is formed from a flexible polymer such as is commonly used in medical tubing and is of a constant inner and outer diameter. A plug 78' is secured within the distal end of inner rod 76' adjacent the detachable distal end 75' of the outer sleeve 74'. Mixing paddle 79 is connected to the distal end 75' of sleeve 74' and functions in a similar manner as described earlier. In use, after the constituent components of the bone cement are throughly mixed as discussed earlier, the mixing paddle is drawn to a position adjacent the cap 60. The outer sleeve is bent sufficiently to cause it to break at the score line or notch 73'. During bending of the outer sleeve, the inner rod 76' (made of the flexible polymer tubing) flexes or compresses an amount sufficient to allow the outer sleeve to break. Once the outer rod is broken, the user pulls on handle 71' which is connected to inner rod 76' by an adapter as illustrated. As the handle, inner rod and the remaining outer sleeve are pulled away, the distal plug 78' is pulled from the center of mixing paddle 79 to allow cement to exit therethrough.

Figure 8:
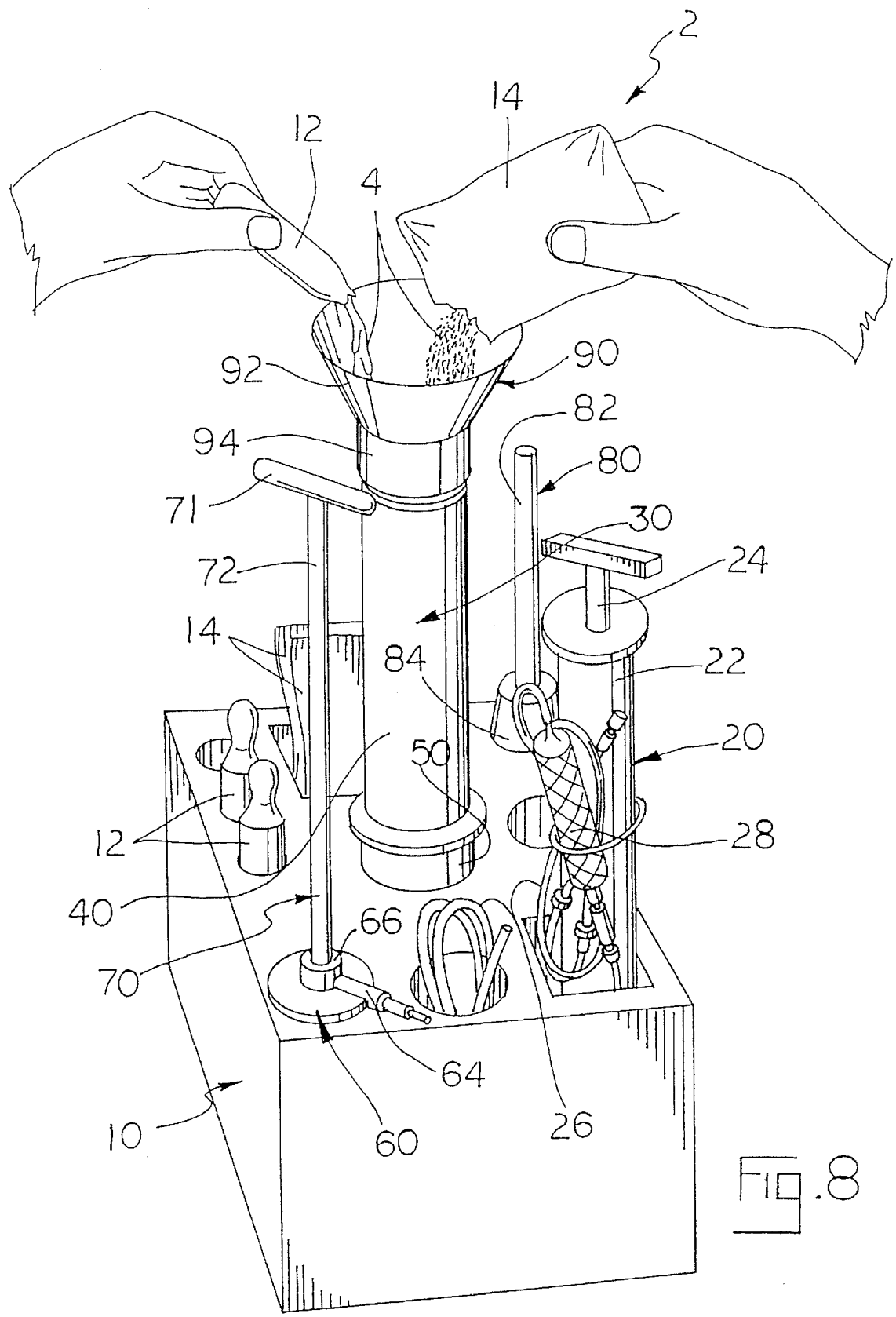
FIG. 8 is a perspective view of the kit of this invention showing the liquid and powder constituent components being poured into the mixing cartridge through a funnel attachment connected to the cartridge.

As shown in FIGS. 1, 10 and 11, cement nozzles 80 are of conventional design and include an elongated neck 82 and a coupling part 84, which is adapted to be fitted to outlet port 66 of cap 60. As shown in FIGS. 1 and 8, funnel attachment 90 includes a conical flange 92 and an annular neck 94. Neck 94 has a threaded inner surface (not shown), which allows the funnel to be connected to the proximal end of cartridge 30.

Figure 9:
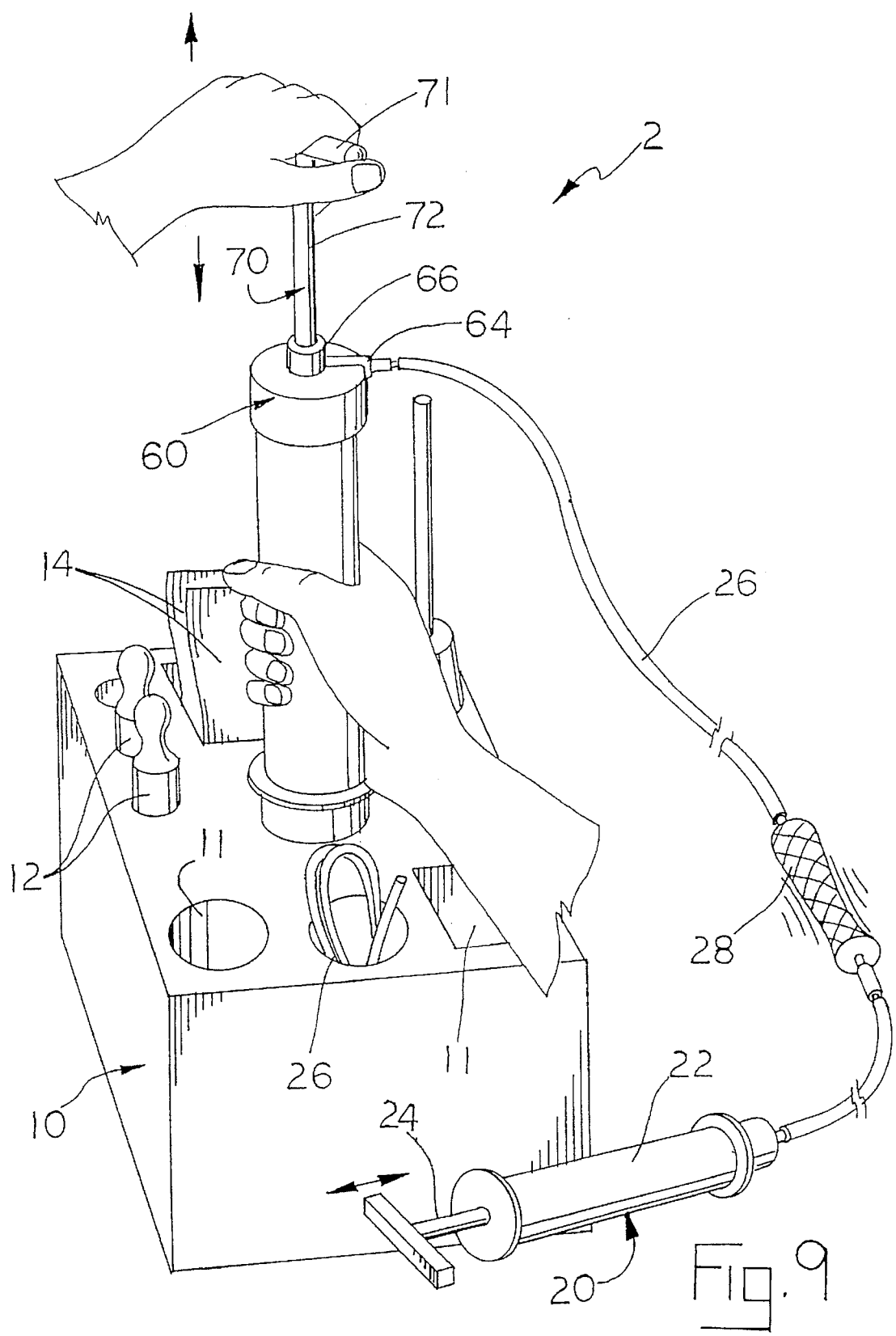
FIG. 9 is a perspective view of the kit of this invention showing the cap connected to the mixing cartridge for facilitating mixing of the constituent components and the vacuum pump connected to the cap for drawing a vacuum in the cartridge.

FIGS. 8–11 demonstrate the use of kit 2 in the preparation of bone cement. Kit 2 is packaged in an external packaging (not shown) with funnel attachment 90 connected to cartridge 30. One will notice that cartridge 30 is packaged in tray 10 in its extended mixing position for the convenience of the user. As shown in FIG. 8, the cement constituent components 4 of the cement are poured into mixing cylinder 30 through funnel 90. Once the proper volumes of the various constituent components 4 of the cement have been poured into the cartridge, funnel attachment 90 is removed and discarded. Cap 60 is then removed from tray 10 and attached to cartridge 30. Vacuum pump 20, tubing 26, and vacuum indicator 28 are also removed from tray 10 and connected to valve port 64 of cap 60. Once cap 60 and vacuum pump 20 are connected to cartridge 30 as shown in FIG. 9, a vacuum is drawn within cartridge 30 by manually reciprocating shaft 24 of vacuum pump 20. Vacuum indicator 28 collapses to indicate that the cartridge is at the desired vacuum pressure. The vacuum pump may then be removed and the vacuum is maintained by a one-way check valve (not shown) within cap 60. The constituent components 4 of the cement are then mixed by manually reciprocating agitator 70 in a manner well known in the art. When the constituent components 4 of the cement have been thoroughly mixed, agitator part 70 is pulled to its outer limit so that agitator paddies 79 abut against cap 60.

As shown in FIGS. 10 and 11, the vacuum pressure within cartridge 30 is then released and cartridge 30 is compressed for use in a cement injector gun (not shown). To release the vacuum pressure within cartridge 30, inner cylinder 50 is rotated and axially compressed within outer cylinder 40 from its extended position to its intermediate vacuum release position. Inner cylinder 50 is rotated within outer cylinder 40 to move key 46 through lateral end section 57 into longitudinal section 54 so that the inner cylinder can be compressed. With key 46 aligned with section 57, the inner cartridge is in its vacuum release and collapsing position. In the vacuum release position, the position of inner cylinder 50 within outer cylinder 40 locates O-rings 52, which provide the hermetic seal between the inner and outer cylinder 40, 50, between the opposed ends of grooves 41 formed in the outer cylinder 40. Grooves 41 provide an air passage into the interior of cartridge 30 around O-rings 52 through channels 41.

To release the vacuum pressure within cartridge 30 in the alternative embodiment of FIG. 3A, inner cylinder 50 is rotated and axially compressed within outer cylinder 40 from its extended position to its intermediate vacuum release position. Inner cylinder 50 is rotated within outer cylinder 40 to move key 46 through lateral end section 57' into longitudinal section 56 so that the inner cylinder can be compressed. The axial compression of inner cylinder 50 within outer cylinder 40 is arrested at its intermediate vacuum release position when key 46 reaches intermediate lateral section 55'. In the vacuum release position, the position of inner cylinder 50 within outer cylinder 40 locates O-rings 52, which provide the hermetic seal between the inner and outer cylinder 40, 50, between the opposed ends of grooves 41 formed in the outer cylinder 40. Grooves 41 provide an air passage into the interior of cartridge 30 around O-rings 52 through channels 41. Once the pressure within cartridge 30 has been equalized, inner cylinder 40 is rotated again to move key 46 along lateral intermediate section 55 into longitudinal section 54'. Now inner cylinder 50 can be completely compressed into outer cylinder 40 to its retracted position.

Once cartridge 30 is compressed into its retracted position, distal end 75 of sleeve 74 of the agitator is broken off and discarded as shown in FIGS. 6 and 7. When agitator 70 is broken off, plug 78 is pulled from the cap and outlet port 66 is opened. The suitable cement nozzle 80 can now be affixed to outlet port 66, and cartridge 30 inserted into the applicator gun (not shown).

It is understood that the above description does not limit the invention to the details given, but may be modified within the scope of the following claims.

I claim:

1. An apparatus for manufacturing bone cement by mixing a plurality of constituent components and for delivering the same, said apparatus comprising:

a cartridge including a tubular cylinder having an open proximal end and a distal end;

a cap connectable to said cylinder proximal end, said cap including means for connecting said cartridge to a vacuum pump to draw a vacuum within said cartridge, said cap defining an opening therethrough;

a piston plug shiftably disposed within said cylinder for axial movement within said cylinder towards said cap to expel cement from said cartridge;

agitator means for mixing the constituent components of the bone cement within said cartridge, said agitator means including an elongated shaft having a detachable tubular distal end reciprocally received through said cap opening, and a paddle connected to said shaft distal end for axial reciprocation within said cartridge;

end plug means extending from the shaft into the shaft distal end; and frangible means disposed in said shaft for breaking away and detaching said shaft distal end from said shaft and removing said end plug means from said shaft distal end;

whereby the bone cement can be expelled through said shaft distal end.

2. The apparatus of claim 1 wherein said end plug means comprises a dumbbell shaped end plug integrally connected to said shaft and disposed within said shaft distal end, said end plug including a flexible middle for permitting said shaft distal end to be axially bent whereby said shaft distal end is severed from said shaft when said shaft distal end is disposed within said cap opening.

3. The apparatus of claim 1 wherein said detachment means includes a flexible inner rod axially carried within the elongated shaft wherein a distal end of the flexible inner rod constitutes said end plug means.

4. An apparatus for manufacturing bone cement by mixing a plurality of constituent components and for delivering the same, said apparatus comprising:

a cartridge;

a cap connectable to said cartridge, said cap including means for connecting said cartridge to a vacuum pump to draw a vacuum within said cartridge, said cap having an opening defined therein for expelling cement from said cartridge;

a piston plug shiftably disposed within said cartridge for axial movement within said cartridge towards said cap to expel said cement from said cartridge;

agitator means for mixing said constituent components of the bone cement within said cartridge, said agitator means including an elongated shaft having a detachable tubular distal end reciprocally received through said cap opening, and a paddle connected to said shaft distal end for axial reciprocation within said cartridge; and frangible means disposed in said shaft for breaking away and detaching said shaft distal end from said shaft;

whereby said cement can be expelled through said shaft distal end.

5. The apparatus of claim 4 wherein said detachment means includes a dumbbell shaped end plug integrally connected to said shaft and disposed within said shaft distal end, said plug including a flexible middle for permitting said shaft distal end to be axially bent whereby said shaft distal end is severed from said shaft when said shaft distal end is disposed within said cap opening.

6. An apparatus for manufacturing bone cement by mixing a plurality of constituent components and for delivering the same, said apparatus comprising:

a cartridge including a tubular cylinder having an open proximal end and a distal end;

a cap connectable to said cylinder proximal end, said cap including means for connecting said cartridge to a vacuum pump to draw a vacuum within said cartridge, said cap defining an opening therethrough;

a piston plug shiftably disposed within said cylinder for axial movement within said cylinder towards said cap to expel cement from said cartridge;

agitator means for mixing the constituent components of the bone cement within said cartridge, said agitator means including an elongated shaft having a detachable tubular distal end reciprocally received through said cap opening, and a paddle connected to said shaft distal end for axial reciprocation within said cartridge;

end plug means extending from the shaft into the shaft distal end; and frangible means disposed in said shaft for breaking away and detaching said shaft distal end from said shaft and removing said end plug means from said shaft distal end;

whereby the bone cement can be expelled through said shaft distal end; and wherein said end plug means comprises a dumbbell shaped end plug integrally connected to said shaft and disposed within said shaft distal end, said end plug including a flexible middle portion for permitting said shaft distal end to be axially bent whereby said shaft distal end is severed from said shaft when said shaft distal end is disposed within said cap opening.

7. An apparatus for manufacturing bone cement by mixing a plurality of constituent components and for delivering the same, said apparatus comprising:

a cartridge including a tubular cylinder having an open proximal end and a distal end;

a cap connectable to said cylinder proximal end, said cap including means for connecting said cartridge to a vacuum pump to draw a vacuum within said cartridge, said cap defining an opening therethrough;

a piston plug shiftably disposed within said cylinder for axial movement within said cylinder towards said cap to expel cement from said cartridge;

agitator means for mixing the constituent components of the bone cement within said cartridge, said agitator means including an elongated shaft having a detachable tubular distal end reciprocally received through said cap opening, and a paddle connected to said shaft distal end for axial reciprocation within said cartridge;

end plug means extending from the shaft into the shaft distal end; and frangible means disposed in said shaft for breaking away and detaching said shaft distal end from said shaft and removing said end plug means from said shaft distal end;

whereby the bone cement can be expelled through said shaft distal end; and wherein said detachment means includes a flexible inner rod axially carried within said elongated shaft, and wherein a distal end of said rod constitutes said end plug means.

8. An apparatus for manufacturing bone cement by mixing a plurality of constituent components and for delivering the same, said apparatus comprising:

a cartridge;

a cap connectable to said cartridge, said cap including means for connecting said cartridge to a vacuum pump to draw a vacuum within said cartridge, said cap defining an opening therethrough for expelling cement from said cartridge, a piston plug shiftably disposed within said cartridge for axial movement within said cartridge towards said cap to expel cement from said cartridge;

agitator means for mixing said constituent components of the bone cement within said cartridge, said agitator means including an elongated shaft having a detachable tubular distal end reciprocally received through said cap opening, and a paddle connected to said shaft distal end for axial reciprocation within said cartridge; and frangible means disposed in said shaft for breaking away and detaching said shaft distal end from said shaft;

whereby said cement can be expelled through said shaft distal end; and wherein said detachment means includes a dumbbell shaped end plug integrally connected to said shaft and disposed within said shaft distal end, said end plug including a flexible middle portion for permitting said shaft distal end to be axially bent, whereby said shaft distal end is severed from said shaft when said shaft distal end is disposed within said cap opening.

9. An apparatus for mixing and delivering bone cement, said apparatus comprising:

a tubular cylinder;

a cap on one end of said cylinder and defining an opening therethrough;

a piston disposed in said cylinder for axial movement in said cylinder towards said cap to expel bone cement in said cylinder through said opening;

an agitator for mixing constituent components of the bone cement, said agitator comprising an elongated shaft extending through said cap opening and having a frangible and detachable tubular distal end, and an end plug extending from said shaft into said tubular distal end;

wherein upon break-away detachment of said tubular distal end from said shaft, said end plug is removable from said tubular distal end and the bone cement in said cylinder can be expelled through said tubular distal end in said opening by movement of said piston.

10. An apparatus for mixing and delivering bone cement, said apparatus comprising:

a tubular cylinder;

a cap on one end of said cylinder and defining an opening therethrough;

a piston plug disposed in said cylinder for axial movement in said cylinder towards said cap to expel the bone cement in said cylinder through said opening;

an agitator for mixing components of the bone cement, said agitator comprising an elongated shaft extending through said cap opening, said shaft having a tubular end portion in said cylinder, an outside diameter of said tubular end portion being substantially equal to an inside diameter of said opening, and mixing means fixed to said tubular end portion, such that movement of said shaft causes movement of said mixing means;

wherein upon separation of said tubular end portion and said shaft, with said tubular end portion in said cap opening, said tubular end portion serves as an outlet port for the expulsion of the bone cement from said cylinder in response to movement of said piston plug in said cylinder.

* * * * *